US012661068B2

(12) United States Patent (10) Patent No.: US 12,661,068 B2
Moskovich et al. (45) Date of Patent: Jun. 23, 2026

(54) SYSTEM FOR DENOISING MOTION ARTIFACT SIGNALS AND METHOD THEREOF

(71) Applicant: Neteera Technologies Ltd., Givat Ram (IL)

(72) Inventors: Daniel David Moskovich, Jerusalem (IL); Yochanan Steinberg, Oak Park, MI (US); Lior Weizman, Jerusalem (IL)

(73) Assignee: Neteera Technologies Ltd., Givat Ram (IL)

( * ) Notice: Subject to any disclaimer, the term of this patent is extended or adjusted under 35 U.S.C. 154(b) by 739 days.

(21) Appl. No.: 17/634,796

(22) PCT Filed: Aug. 12, 2020

(86) PCT No.: PCT/IL2020/050882
§ 371 (c)(1),
(2) Date: Feb. 11, 2022

(87) PCT Pub. No.: WO2021/028915
PCT Pub. Date: Feb. 18, 2021

(65) Prior Publication Data
US 2022/0287645 A1 Sep. 15, 2022

Related U.S. Application Data

(60) Provisional application No. 62/885,825, filed on Aug. 13, 2019.

(51) Int. Cl.
*A61B 5/00* (2006.01)
*A61B 5/02* (2006.01)
(Continued)

(52) U.S. Cl.
CPC ........ *A61B 5/7207* (2013.01); *A61B 5/02007* (2013.01); *A61B 5/02055* (2013.01);
(Continued)

(58) Field of Classification Search
CPC .............. A61B 5/7207; A61B 5/02007; A61B 5/02055; A61B 5/02108; A61B 5/02405;
(Continued)

(56) References Cited

U.S. PATENT DOCUMENTS 10,278,647 B2 5/2019 Salehizadeh et al.
2005/0187433 A1 8/2005 Horn et al.
(Continued)

FOREIGN PATENT DOCUMENTS

WO WO 2018/077774 A1 5/2018

OTHER PUBLICATIONS

Extended European Search Report (EESR) dated Oct. 20, 2023 issued by the EPO for corresponding EP Application No. 20853039.4.
(Continued)

*Primary Examiner* — Niketa Patel
*Assistant Examiner* — Skylar Lindsey Christianson
(74) *Attorney, Agent, or Firm* — Meitar Patents Ltd.; Daniel Kligler

(57) ABSTRACT

The present invention provides a system and a method for denoising motion artifacts from vital signs signals comprising steps of receiving one or more reflected signals from at least one subject, generating a time sequence buffer of reflected signals of predefined duration for vital signals processing, source separation and a component selection, and estimating and tracking vital signs of the source separation and a component selection.

8 Claims, 8 Drawing Sheets

Figure 1:
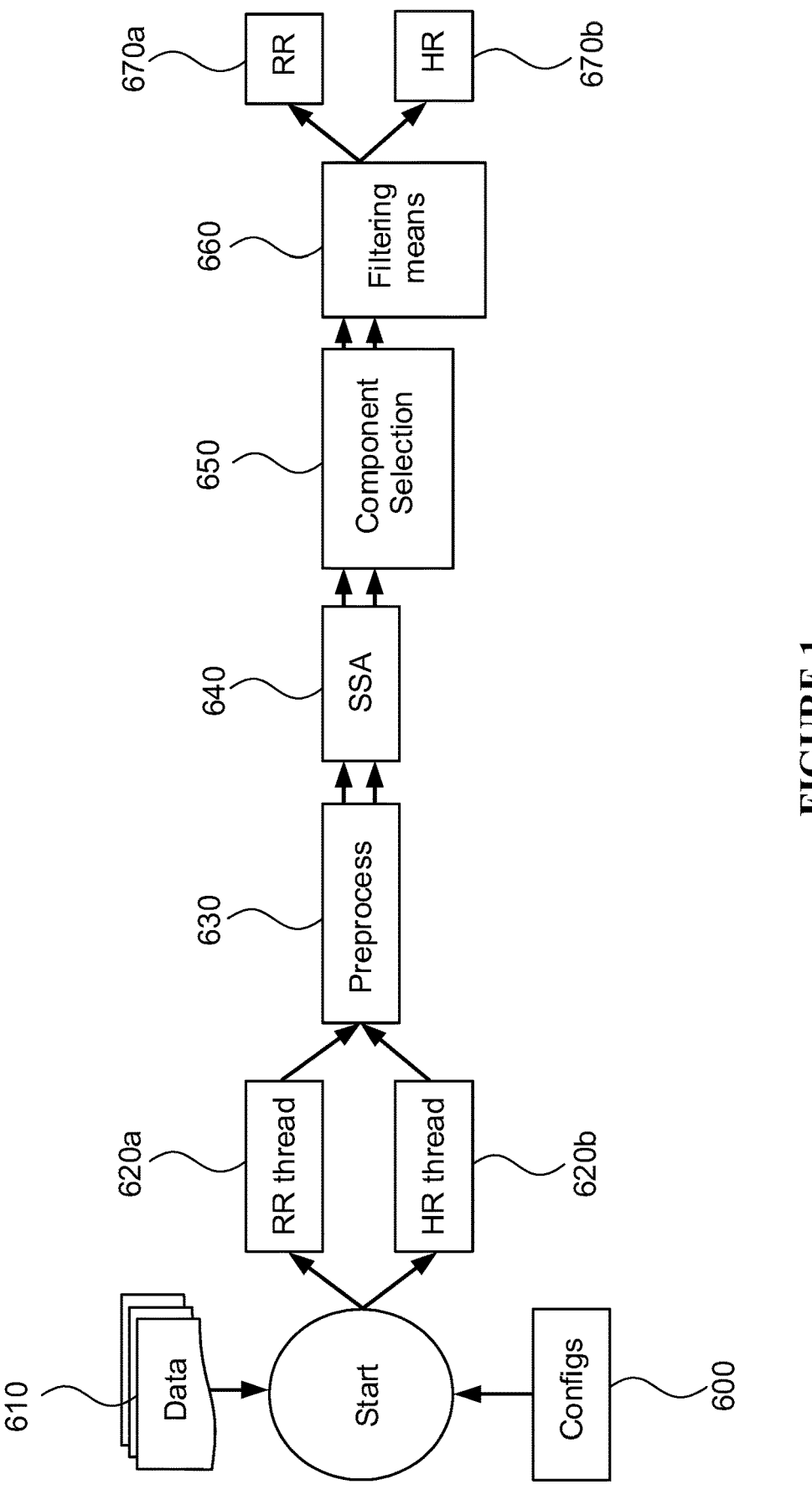

(51) Int. Cl.

| | |
|---|---|
| *A61B 5/0205* | (2006.01) |
| *A61B 5/021* | (2006.01) |
| *A61B 5/024* | (2006.01) |
| *A61B 5/029* | (2006.01) |
| *A61B 5/0507* | (2021.01) |
| *A61B 5/08* | (2006.01) |
| *A61B 5/11* | (2006.01) |

(52) U.S. Cl.

CPC ...... *A61B 5/02108* (2013.01); *A61B 5/02405* (2013.01); *A61B 5/029* (2013.01); *A61B 5/0507* (2013.01); *A61B 5/0816* (2013.01); *A61B 5/1102* (2013.01); *A61B 5/7225* (2013.01)

(58) Field of Classification Search

CPC ..... A61B 5/029; A61B 5/0507; A61B 5/0816; A61B 5/1102; A61B 5/7225

See application file for complete search history.

(56) References Cited

U.S. PATENT DOCUMENTS

| | | | |
|---|---|---|---|
| 2008/0146890 A1 | 6/2008 | Leboeuf et al. | |
| 2010/0152600 A1* | 6/2010 | Droitcour ............ | A61B 5/7221 |
| | | | 600/534 |
| 2014/0276099 A1 | 9/2014 | Kirenko et al. | |
| 2016/0198964 A1 | 7/2016 | Lee et al. | |
| 2019/0178980 A1* | 6/2019 | Zhang ................. | A61B 5/7267 |
| 2019/0192079 A1* | 6/2019 | Groenendaal ...... | A61B 5/02433 |

OTHER PUBLICATIONS

Xie Kai et al "Non-contact Heart Rate Monitoring for Intensive Exercise Based on Singular Spectrum Analysis"; 2019 IEEE Conf MIPR, pp. 228-233.

Corresponding International Patent Application No. PCT/IL2020/050882 International Search Report dated Apr. 12, 2021.

Corresponding Australian Patent Application No. AU 2020327715 Examination Report dated Mar. 16, 2022.

* cited by examiner

SYSTEM FOR DENOISING MOTION ARTIFACT SIGNALS AND METHOD THEREOF

CROSS-REFERENCE TO RELATED APPLICATIONS

This application is a national phase application filed under 35 U.S.C. § 371 of International Patent Application No. PCT/IL2020/050882, filed on Aug. 12, 2020, which claims the benefit of priority to U.S. Provisional Patent Application No. 62/885,825, filed on Aug. 13, 2019, each of the foregoing applications incorporated herein in their entirety by reference.

FIELD OF THE INVENTION

The present invention pertains to a system and a method of removing noise and motion artifact signals from vital signals data sets obtained from one or more objects. More particularly, the present invention pertains to a system and a method of removing noise and motion artifact signals from vital signals data for vital signs enhancement.

BACKGROUND OF THE INVENTION

A variety of vital sign measurements namely heart rate detection devices suffer from motion artifacts, especially in the case where the spatial and temporal scales of the motion are like or beyond those of the heart rate related signals being measured.

During acquisition of vital signs signals different noises like instrument noise, muscle spasms, external or subject motion artifacts and baseline wander frequently contaminate and degrade the vital sign information. Current solutions to mitigate the effects of undesired noise often rely on a variety of standard signal processing tools or include the use of an additional sensor information such as a motion sensor or to increase the observation time or simply reacquire vital sign measurements under more favorable conditions.

In cases where the added noise is overwhelming, typical heart rate monitor devices either display the wrong heart rate value or no heart rate value at all. This is regarded to be a major disadvantage since the measurement results in an inaccurate or non-displayed heart rate.

Therefore, there is a long felt unmet need for a system and method which will be able to provide clear, accurate real time vital signal information while being robust against any motion or system induced contaminating noise.

SUMMARY OF THE INVENTION

It is an object of the present invention to disclose a computerized method for denoising motion from vital signs signals comprising steps of:
a. receiving one or more reflected signals from at least one subject;
b. generating a time sequence buffer of reflected signals of predefined duration for vital signals processing;
c. source separation and a component weighting; and
d. estimating and tracking vital signs of the source separation and a component weighting.

It is another object of the present invention to disclose the method as mentioned in any of the above, wherein the source separation and component selection further comprising steps of:

a. signal decomposition of pre-processed buffered signals via singular spectrum analysis; spectral computation of separated components;
b. component weighting of the decomposed components;
c. forming a probability density function from weighted components; and
d. computation of vital signs from weighted probability density function.

It is another object of the present invention to disclose the method as mentioned in any of the above, wherein the step of estimating and tracking vital signs via tracking filter.

It is another object of the present invention to disclose the method as mentioned in any of the above, wherein the vital signals are selected from the group consisting of: heart rate (HR), heart rate interval (HRI), respiratory rate (RR), heart rate variability (HRV), respiration amplitude, (RA), respiration amplitude variability, respiration rate variability (RRV), ballistocardiogram (BCG), BCG amplitude variability, pulse wave velocity (PWV), blood pressure (i.e. MAP, systolic and diastolic), vascular resistance, body temperature, pulse pressure variability, stroke volume and variability and any combination thereof.

It is another object of the present invention to disclose a non-transitory computer readable medium comprising instructions for denoising non-vital signals:
a. receiving one or more reflected signals from at least one subject;
b. generating a time sequence buffer of reflected signals of predefined duration for vital signals processing;
c. pre-processing the buffered signals by processor means via filtering and decimation;
d. source separation and a component weighting; and
e. estimating and tracking vital signs of the source separation and a component weighting.

It is another object of the present invention to disclose the method as mentioned in any of the above, wherein the source separation and component selection further comprising steps of:
a. signal decomposition of pre-processed buffered signals via singular spectrum analysis; spectral computation of separated components;
b. component weighting of the decomposed components;
c. forming a probability density function from weighted components;
d. computation of vital signs from weighted probability density function; and
e. filter tracking of vital signs value.

It is another object of the present invention to disclose a system for denoising non vital signals comprising:
a. a decomposition component for decomposing data to spectral components;
b. Singular Spectral Analysis (SSA) component configured for component weighting of said decomposed components;
c. an estimation component for identifying vital signs from spectral content of the weighted decomposed component; and
d. a filtering component for extracting heart rate (HR) signal and respiration rate (RR) signal output.

It is another object of the present invention to disclose the system as mentioned in any of the above, wherein the vital signals are selected from the group consisting of: heart rate (HR), respiratory rate (RR), heart rate variability (HRV), heart rate interval (HRI), respiration amplitude, (RA), respiration amplitude variability, respiration rate variability (RRV), ballistocardiogram (BCG), BCG amplitude variability, pulse wave velocity (PWV), blood pressure (i.e. MAP, systolic and diastolic), vascular resistance, body temperature, pulse pressure variability, stroke volume and variability and any combination thereof.

It is another object of the present invention to disclose the system as mentioned in any of the above, wherein additionally comprising transceiver means for transmitting and/or receiving in real-time one or more signals from one or more subjects.

It is another object of the present invention to disclose a device comprising a non-transitory computer readable medium comprising instructions for denoising non-vital signals:

a. receiving one or more reflected signals from at least one subject;

b. generating a time sequence buffer of reflected signals of predefined duration for further vital signals processing;

c. pre-processing the buffered signals by processor means via filtering and decimation;

d. source separation and a component weighting; and e. estimating and tracking vital signs of the source separation and a component weighting.

It is another object of the present invention to disclose the device as mentioned in any of the above, wherein the vital signals are selected from the group consisting of: heart rate (HR), respiratory rate (RR), heart rate variability (HRV), heart rate interval (HRI), respiration amplitude, (RA), respiration amplitude variability, respiration rate variability (RRV), ballistocardiogram (BCG), BCG amplitude variability, pulse wave velocity (PWV), blood pressure (i.e. MAP, systolic and diastolic), vascular resistance, body temperature, pulse pressure variability, stroke volume and variability and any combination thereof.

It is another object of the present invention to disclose the device as mentioned in any of the above, wherein the source separation and component selection further comprising steps of:

a. signal decomposition of pre-processed buffered signals via singular spectrum analysis; spectral computation of separated components;

b. component weighting of said decomposed components;

c. forming a probability density function from weighted components;

d. computation of vital signs from weighted probability density function; and, e. filter based tracking of vital signs value.

It is another object of the present invention to disclose the device as mentioned in any of the above, wherein additionally comprising transceiver means for transmitting and/or receiving in real-time one or more signals from one or more subjects.

BRIEF DESCRIPTION OF THE INVENTION

Figure 2A:
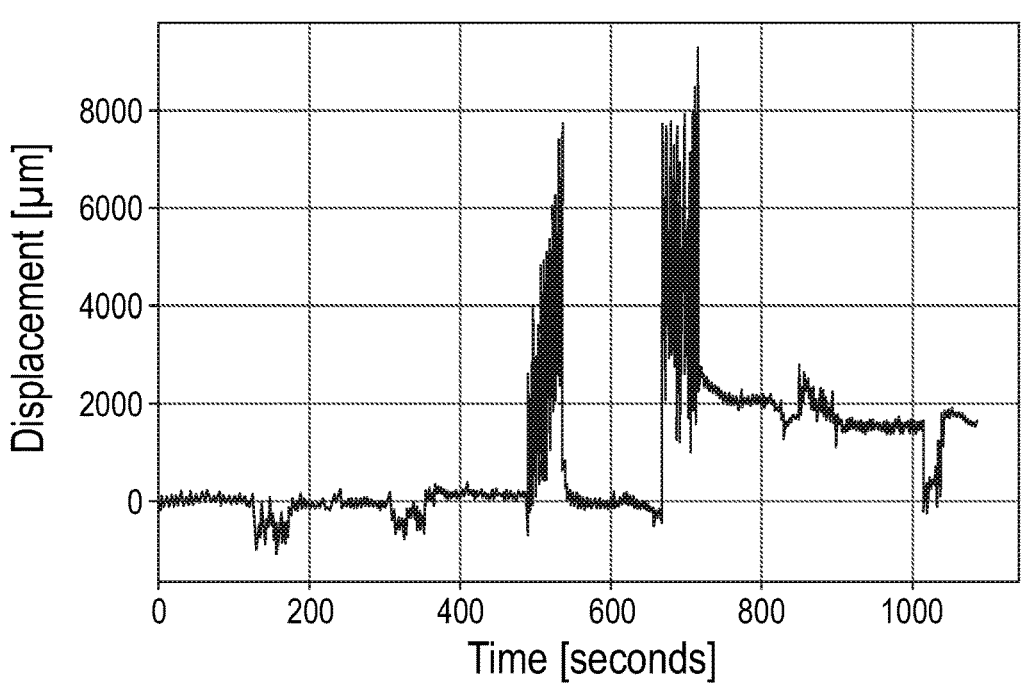
Figure 2B:
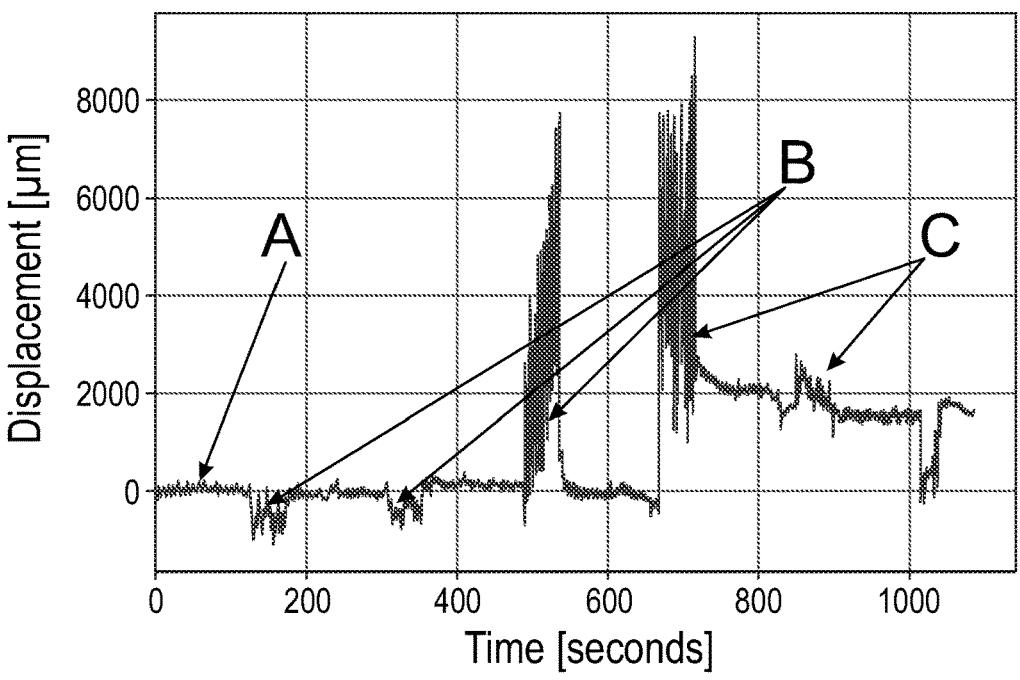
Figure 3:
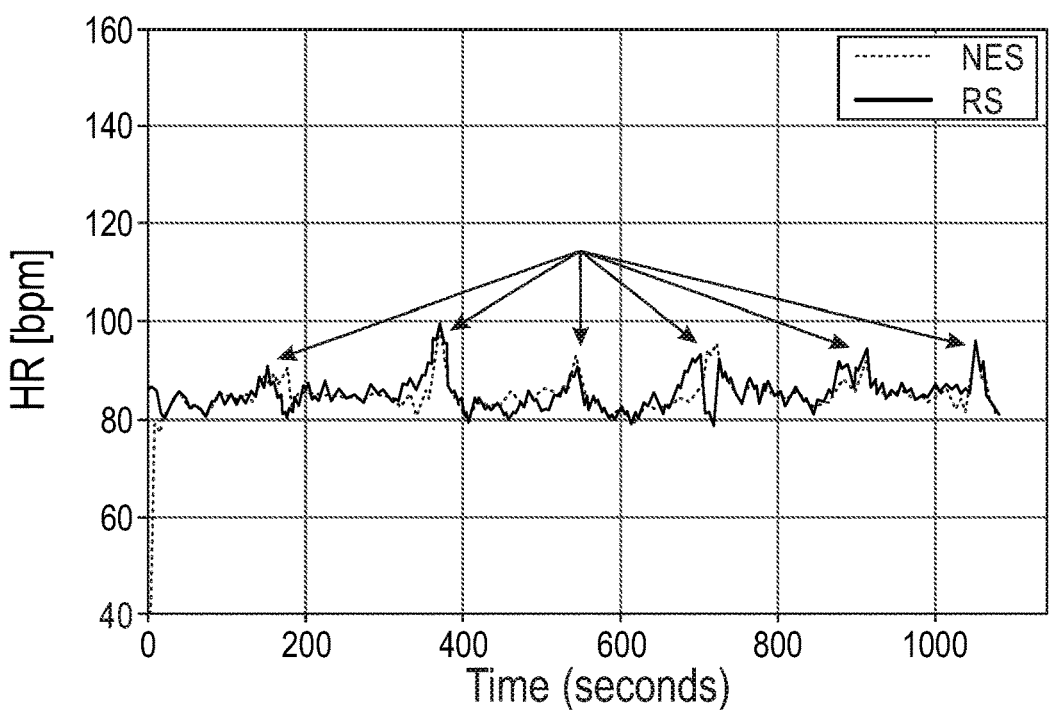
Figure 4:
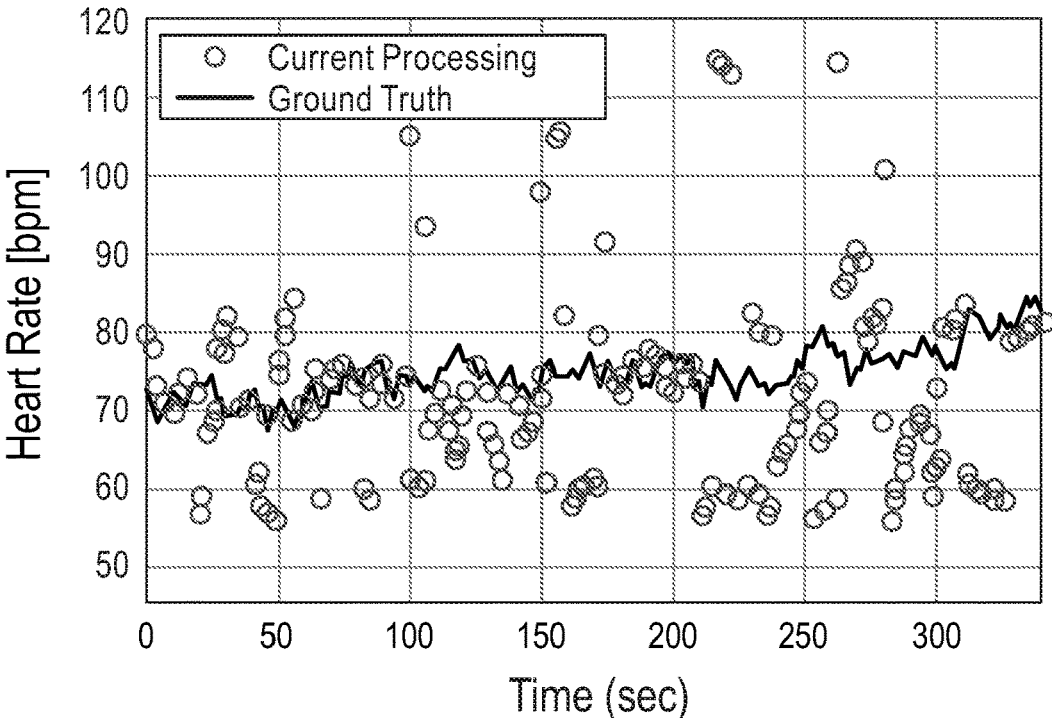
Figures 5, 6A:
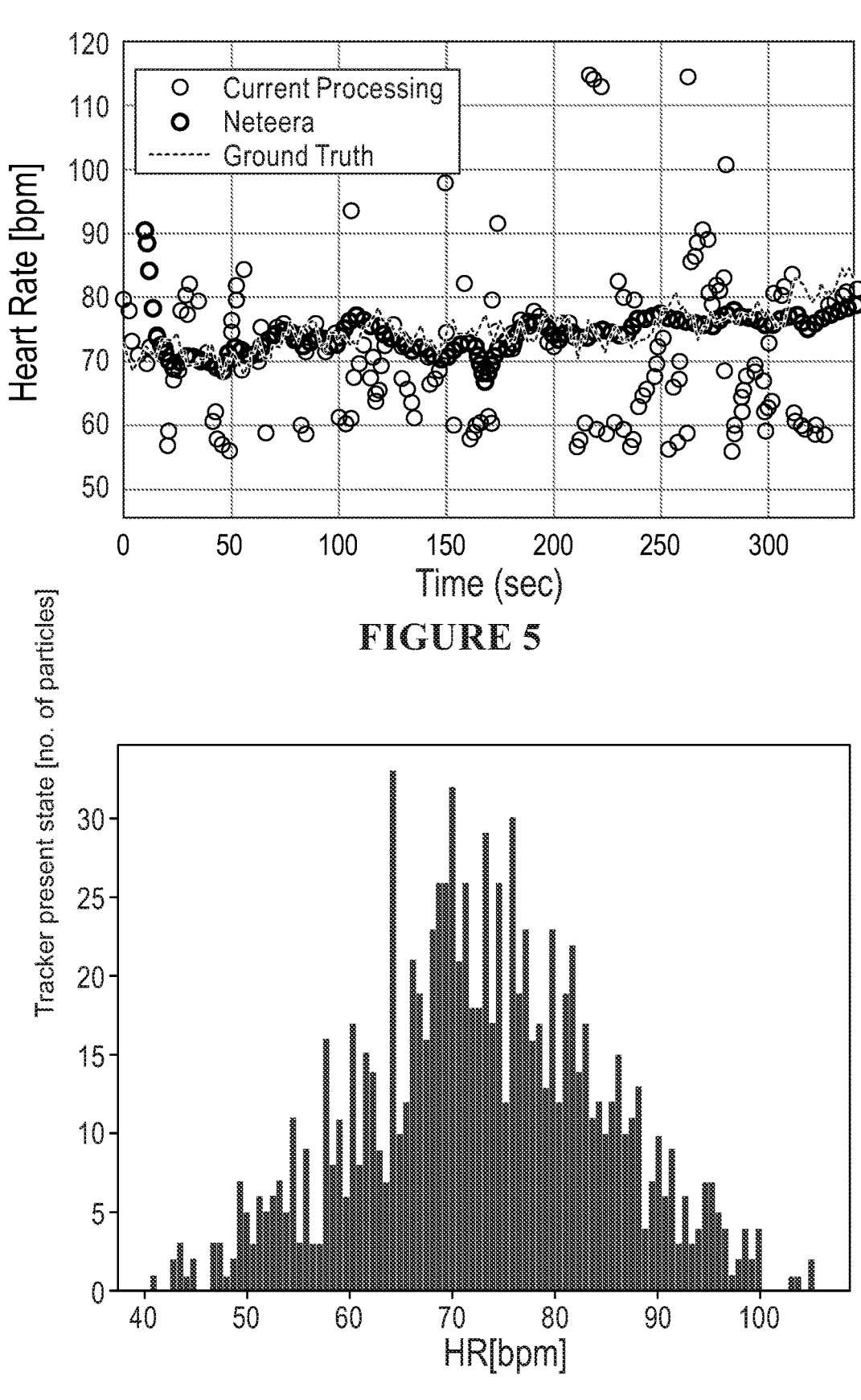
Figures 6B, 6C:
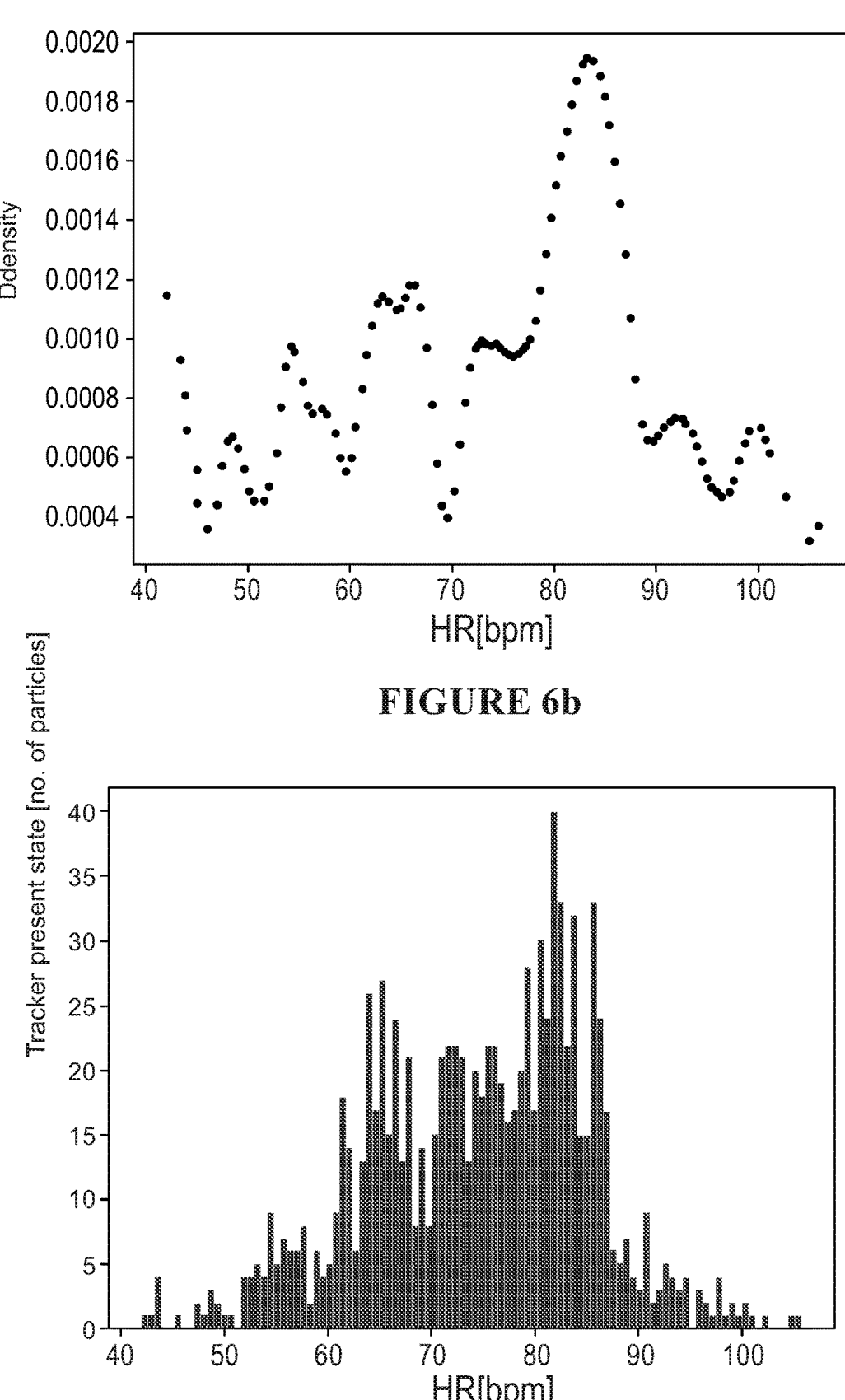
Figure 7:
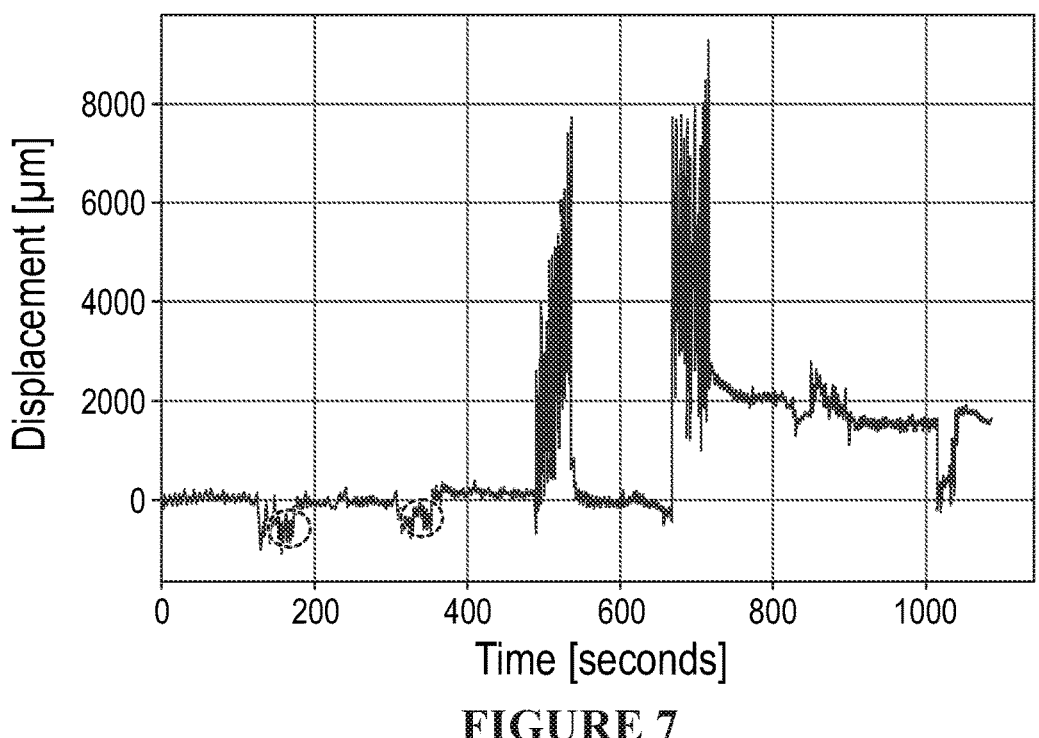
Figure 8:
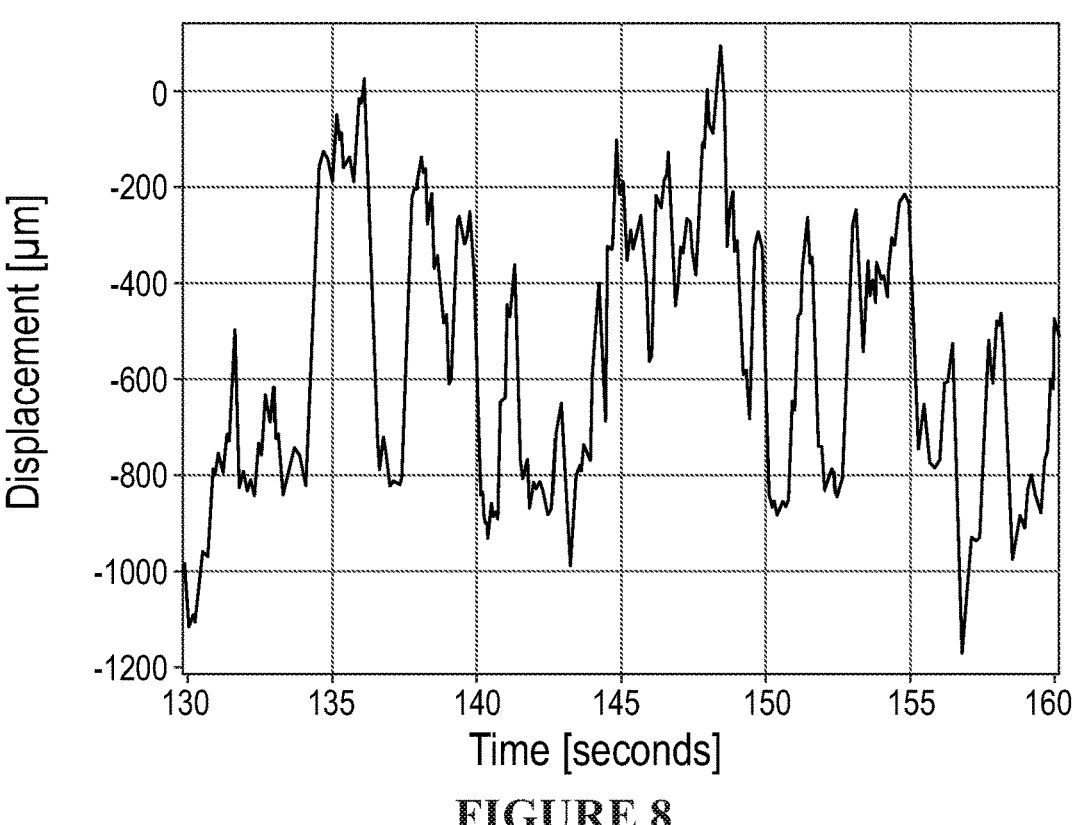
Figure 9:
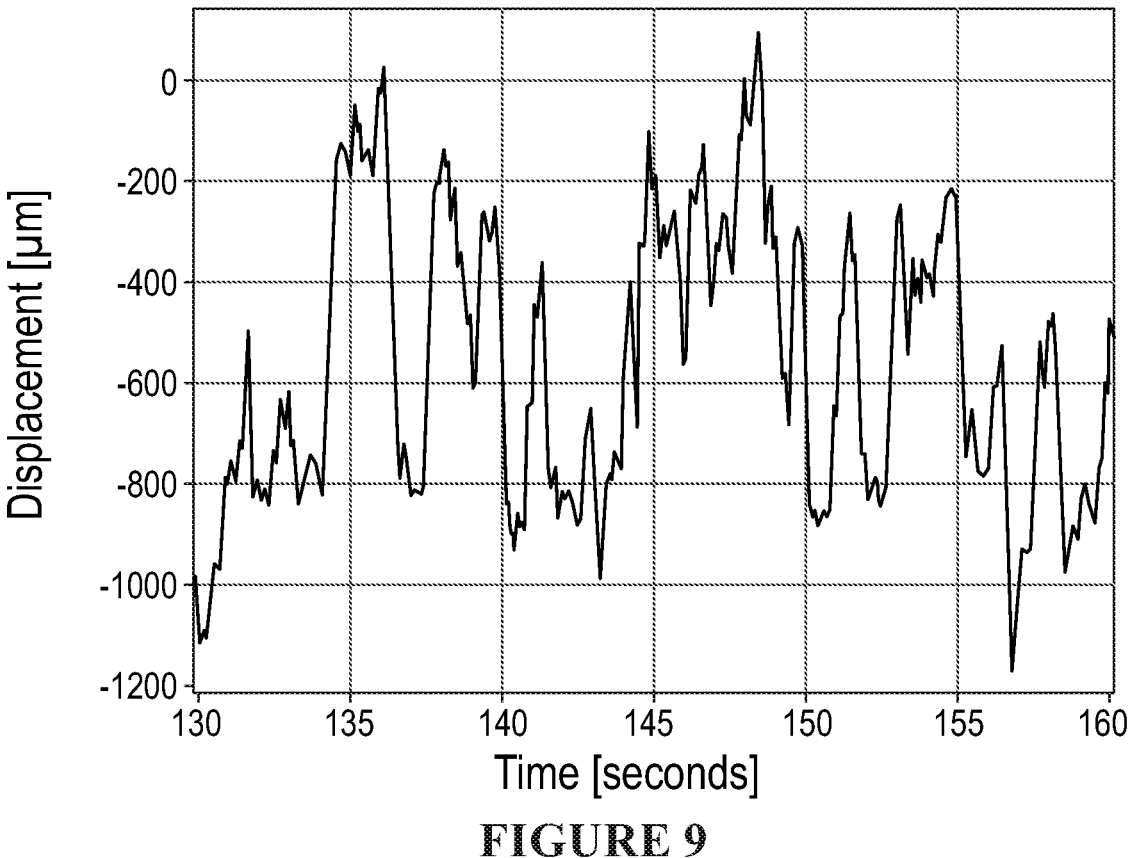
Figure 10:
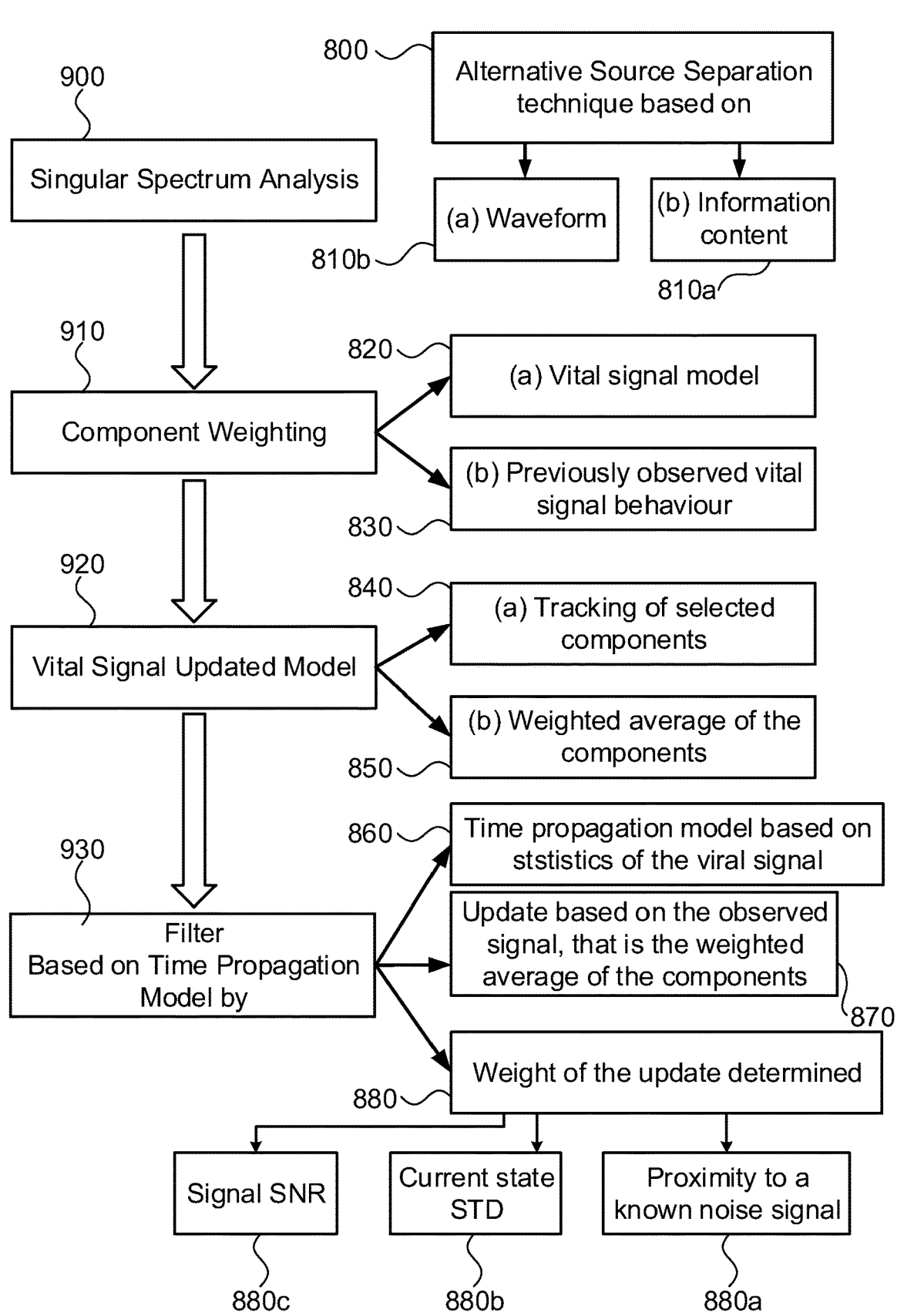

In order to better understand the invention and its implementation in practice, a plurality of embodiment will now be described, by way of non-limiting example only, with reference to the accompanying drawings, wherein:

FIG. 1 presents schema of a system for denoising the non-vital signals, according to an exemplary embodiment of the disclosure;

FIGS. 2a-b present a graph of an example of input data, displayed as displacement data of a subject from a radar, according to an exemplary embodiment of the disclosure;

FIG. 3 presents a graph of the subject measured heart rate by the system for denoising non-vital signals compared with a certified ECG, according to an exemplary embodiment of the disclosure;

FIG. 4 presents a graph of naïve heart rate detection using spectral-based means that does not use motion denoising, according to an exemplary embodiment of the disclosure;

FIG. 5 presents a graph of heart rate detection using the SSA based processing system, according to an exemplary embodiment of the disclosure;

FIGS. 6a-c present several graphs displaying outputs of steps in the motion denoising method, according to an exemplary embodiment of the disclosure FIGS. 7-9 present examples of input data, displayed as displacement data of a subject from a radar, according to an exemplary embodiment of the disclosure; and FIG. 10 presents a flowchart of the denoising motion contaminated signal, according to an exemplary embodiment of the disclosure.

DETAILED DESCRIPTION OF THE INVENTION

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a method, a computer-implemented system and a computerized system for denoising the noise components which are non-vital sign signals by a modified singular spectrum analysis (SSA) mechanism, therefore, to enhance and extract accurate vital sign information.

The computerized system may be combined with RF based module or transceiver means such as a radar-based system, a phased array-based system, MIMO-based system, MMIC-based system, an electronic based system, an optical-based system, or any acoustical, mechanical or electrostatically based sensing/sensor means preforming remotely in a contact or contact-free manner.

The computerized system combined with transceiver means is configured to track the micro motions of the skin surface of the subject, BCG detection, due to the activity of the lung and heart functions. The computerized system is based on an algorithm that is robust against motion artifacts and providing correct estimation of nomially time averaged vital sign parameters. The performance of the system may be based on a source separation mechanism, relative weighting of a variety of sources, and vital signs tracking capabilities of motion contaminated data. The estimating and tracking vital signs may be via a tracking filter.

The term vital signal refers to one or more vital signs signals which are reflected from the subject body. A signal may further refer to body movement derived from vocal cord vibration, eye movement, body or skin movement due to speech, motion classification such as speaking or singing, change in voice sound, micro skin motions and body motion (such as seizures, tremors, shaking, trembling and/or vibrating).

The term 'Vital signs' herein refers to any physiological indicator, cardiac or pulmonary metrics, medical condition, health indicator or health characteristics such as heart rate (HR), respiratory rate (RR), heart rate variability (HRV), heart rate interval (HRI), respiration amplitude, (RA), respiration amplitude variability, respiration rate variability (RRV), ballistocardiogram (BCG), BCG amplitude variability, pulse wave velocity (PWV), blood pressure (i.e. MAP, systolic and diastolic), vascular resistance, body temperature, pulse pressure variability, stroke volume and variability.

The term 'Subject' herein refers to at least one individual, an object or a living being such as a driver, a passenger, a patient, an adult, an infant, a toddler, a baby, a child, an elderly subject, an occupant, an animal or any desired subject to be detected in a predefined space.

The present invention is based upon empirically determined component selection rules and weighted average of weighted components into new signal based upon degree of motion Reference is now made to FIG. 1 which presents a flowchart of the vital signs source separation processing method and system of the present invention.

The flowchart presents the system configuration 600, data collection 610 comprising HR thread 620a and RR thread 620b. The system further comprises preprocessor module 630 which is comprised of the following steps: mirrored signal, band pass filter, decimation, and removal of mirrored portions of signals.

The method further comprising the source separation module via singular spectrum analysis (SSA) 640, however other source separation techniques could also be utilized such as empirical mode decomposition, independent component analysis, and other similar approaches.

The method further comprising the steps of component selection 650 based upon by following set of rules, namely: existence, band limited power, and localized distribution.

The method further comprising the steps of tracking via a Kalman filter or an extended Kalman filter or unscented Kalman filter or a particle filter 660, or by other classes of models of similar types of techniques for extracting vital sign outputs (i.e. HR 670a and/or RR 670b, based output).

In another embodiment of the present invention, the motion compensation processing method is based on a source separation technique which enables the vital-sign-information to be distinguishable from the unwanted effects due to random motion and noise. Firstly, the raw data are preprocessed prior to entering the motion compensation algorithm This consists of band passing and down sampling the signal. The initial step of the main motion compensation processing method begins with singular spectrum analysis to decompose the raw data into fundamental/spectral components. These resulting signals are further examined in the spectral domain wherein an empirically determined set of features and requirements are used to weighting (e.g. accept or reject) the decomposed components. Based upon the weighting method, the components are recombined to form a new signal whose Fourier transform may be interpreted as a probability density function of desired vital sign information.

The probability density function is transformed into the initial distribution for HR estimation by summing integer multiples of x-axis values with weighting determined by empirical observation of the harmonic structure of the vital sign signal.

This result is provided to a nonlinear estimation filter that is used to track the mean of the probability density function resulting in vital sign signals tracking. These processing steps allow to provide motion robust vital signs monitoring.

In another embodiments, the spectral components may be decomposed to perform one of a Fourier analysis, a sub-band decomposition, a singular spectrum analysis, a multi-channel and/or nested singular spectrum analysis, and/or an empirical mode decomposition, and/or an entropy-based source separation analysis.

In other embodiments of the present invention, a method and corresponding apparatus employ a time-varying spectral analysis approach for reconstructing vital signal that includes motion artifacts. The motion artifacts may be produced by motion of an apparatus or article of manufacture comprising the processing means, relative to a sensing location. The time-varying spectral analysis-based approach enables the vital signal to be reconstructed with accuracy by suppressing the motion artifacts.

In other embodiments of the present invention, to remove the movement artifacts, an adaptive time-space analysis method maybe used suitable for processing non-linear and non-stationary series. Separation of the breathing from the heartbeat may be carried out using a linear band pass filter with upper cut-off frequencies adjusted to obtain signal harmonics.

The system further comprises estimating HRV for developing alternatives to a direct computation based upon the HRI data. Instead, estimates of HRV may be based upon data driven models that statistically represent the variance of the desired HRV.

In other embodiments of the present invention, since HRV is known to strongly correlate with a subject's general state of wellbeing, short term data interpretation module delivery may further include the capability to classify a subject's fatigue level, stress level, emotional state, physiological state, and the like by utilizing vital signs parameters.

In other embodiment the present invention further provides a device comprising a non-transitory computer readable medium or processor means and/or system-on-chip coupled to the processor for vital signals extraction, by combining one or more received outputs.

In one exemplary embodiment, at least part of the spectral components is weighted with the determined corresponding weight and a vital sign is extracted from the weighted spectral components. In an alternative option, one or more vital sign sub-signals are first extracted from individual spectral components of the at least two detection signals, then the extracted vital sign sub-signals are weighted with the determined weight of the corresponding spectral component, and finally a vital sign is extracted from the weighted vital sign sub-signals.

In other embodiments of the present invention, the non-transitory computer readable medium and/or a central processing unit may be combined with a CW or FMCW mode radar-based device configured to transmit constantly at a single frequency. The reflected signal is mixed with a copy of the transmit signal and a $\pi/2$ phase delayed replica (in-phase and quadrature processing), the baseband output provides fine scale displacement information which can be expressed through the following equation:

$$\Delta x = c\Delta\varphi/4\pi f$$

Where $\Delta x$ is the displacement, c is the speed of light, $\Delta\varphi$ is the change in phase, and f is the carrier frequency.

Reference is now made to FIGS. 2-4 which illustrate the measurements of heart rate of the system of the present invention compared to a certified ECG device.

FIGS. 2a-b present a time series (seconds) of displacement data (μm) for signals reflected by the transceiver means from subject body or tissue siting on a chair in a room mostly at rest and undergoing nominal motions at predefined segmented intervals. FIGS. 2a-b indicates the spatial displacement computed from the phase. As illustrated, the graph presents picks of tracking rest period (A) and motion period peaks (B,C). The transceiver means may be a radar-based system, a phased array-based system, an electronic based system, an optical based system or any sensing/sensor means preforming in a non-contact manner, in the THz and sub-THz range. The graph presents a rest case session mixed with various motion protocols. FIG. 3 presents a graph of computed heart rates (bpm) vs. time (seconds) whilst tracking heart rates in presence of motion signals. As illustrated, the arrows in the graph present the tracking changes in HR during motion periods.

The graph illustrates the capability of the present invention to accurately track a change in heart rate during the presence of motion. This is accomplished by identifying instances of increased motion and modifying the processing algorithm accordingly. The distinction between data without motion and data with additional motion is determined by empirical analysis of the SSA components. For example, motion components may have higher energies or higher eigenvalues. Typical motion free SSA analyzed data are further processed according to an optimal set of parameters for rest case scenarios, while data classified as motion contaminated are further processed according to an alternative set of parameters to optimize HR tracking while in the presence of motion. In another embodiment of the present invention, denoising or removing of motion or noise contaminated vital signs signals in order to enhance the real accurate vital signs signals, may be obtained by using threshold detection mechanism.

Therefore, in exemplary embodiments, the processing system may be configured to measure the received signal quality of the heart rate signals, to calculate the heart rate based on the heart rate signal if the signal quality is above a predefined threshold, and to estimate the heart rate based on the motion signal if the signal quality is below the predefined threshold level.

This may be done by a frequency evaluation of the heart rate signal, which results in a determination of the pulse of the subject.

In another embodiment of the present invention, the system may be configured for vital signs detection operating in high sampling or high-frequency range.

Reference is now made to FIG. 4 which presents a graph of heart rate detection vs. time computed by naïve spectral-based approach compared with a reference system, FDA certified pulse sensor.

Reference is now made to FIG. 5 which presents a graph of heart rate detection vs. time of FIG. 4 using the SSA based processing system during motion scenarios, with the present invention processing system. The bold dotes presents the HR curve tracked by the system of the present invention when compared to the ground truth (dashed line) and current processing signals (light dotes).

Reference is now made to FIGS. 6*a*-*c* which present graphs of HR vs. tracker present state (no. of particles). The graphs present 3 stages of present state as follows: FIG. 6*a* present state of the tracker; FIG. 6*b* updated observation and; FIG. 6*c* updated tracker state based on the new observation from which the new HR is estimated.

Reference is now made to FIG. 7 which presents a graph of spatial displacement with motion contaminated periods. The marked motion contaminated periods of about 30 sec window is further analyzed and calculated by the processing method and system of the present invention. The circled peaks present rest period comprising RR waveform and motion period which are clearly different both in amplitude and period of waveforms.

Reference is now made to FIG. 8 which presents a graph of 30 sec. window of detected respiration of FIG. 9 rest period comprising RR waveform.

Reference is now made to FIG. 9 which presents a graph of 30 sec. window of detected respiration of FIG. 9 motion period clearly different—both in amplitude and period of waveforms.

Reference is now made to FIG. 10 which illustrate the computerized method for denoising motion or noise contaminated vital sign signals comprising steps of:

receiving one or more reflected signals from at least one subject.

The method may further comprise the steps of generating a time sequence buffer of reflected signals of predefined duration for further vital signals processing.

The method may further comprise the steps of pre-processing the buffered signals by processor means via mirroring signals prior to filtering and decimation followed by removing mirrored portions of signals.

The method may further comprise the steps of source separation decomposition of pre-processed buffered signals via singular spectrum analysis.

The method may further comprise the steps of spectral computation of separated components.

The method may further comprise the steps of component weighting of the decomposed components.

The method may further comprise the steps of forming a probability density function from selected components.

The method may further comprise the steps of forming adaptive harmonic weights of the probability density function.

The method may further comprise the steps of computation of vital signs from weighted probability density function.

The method may further comprise the steps of nonlinear tracking of vital sign value.

In other embodiment of the present invention, the method may comprise steps of processing one or more phase signals, one or more amplitude signals or combination thereof to determine an estimate of the fundamental frequency or its corresponding harmonics of the vital signs signals.

In another embodiment of the present invention a system for denoising non vital signals is provided comprising: a mirroring component for preprocessing signals obtained from one or more subject, a decomposition component for decomposing the non-mirrored signals data to spectral components, SSA component configured for component weight of said decomposed components, an estimation component for identifying vital signs from spectral content of the weighted decomposed component and a tracking component for extracting heart rate (HR) signal and respiration rate (RR) signal output.

The information recorded can be wirelessly transmitted and/or communicated with any display device, GUI or electronic device to allow the subject, system user or/and caregivers to observe and manage the information and provide feedback for further progress, diagnostic and treatment.

What is claimed is:

1. A method for removing noise and motion artifacts from radar-derived vital signs signals, the method comprising steps of:

receiving, by a radar transceiver operating in a THz range of 0.1 THz to 10 THz, one or more reflected radar signals in the THz range of 0.1 THz to 10 THz from at least one subject;

sampling the reflected radar signals and storing, in a signal processor, a time sequence buffer of the reflected radar signals of predefined duration for vital signals processing, wherein the time sequence buffer comprises at least 60 to 120 samples;

performing, by the signal processor, signal processing comprising:

source separation decomposition of pre-processed buffered signals via singular spectrum analysis;

spectral computation of separated components;

component weighting of decomposed components;

forming a probability density function from weighted decomposed components;

forming adaptive harmonic weights of the probability density function; and computation of vital signs from a weighted probability density function;

estimating and tracking the vital signs, using a tracking filter implemented in the signal processor, to output tracked vital signs compensated for noise and motion artifacts; and transmitting the tracked vital signs to a display device for observation by at least one of: a subject; a system user; and a caregiver.

2. The method according to claim 1, wherein said vital signals are selected from the group consisting of: heart rate (HR); respiratory rate (RR); heart rate variability (HRV); heart rate interval (HRI); respiration amplitude (RA); respiration amplitude variability; respiration rate variability (RRV); ballistocardiogram (BCG); BCG amplitude variability; pulse wave velocity (PWV); blood pressure (i.e. MAP, systolic and diastolic); vascular resistance; body temperature; pulse pressure variability stroke volume; stroke variability; and any combination thereof.

3. The method according to claim 1, further comprising the step of pre-processing said buffered signals by at least one step of:

mirroring signals; filtering; and decimation.

4. The method according to claim 1, further comprising the step of processing at least one of: at least one phase signal, and at least one amplitude signal, to determine an estimate of fundamental frequency or corresponding harmonics of vital signs signals.

5. A system for removing noise and motion artifacts from radar-derived vital signs signals, the system comprising:

a radar transceiver, configured to: receive one or more reflected radar signals in a THz range of 0.1 THz to 10 THz from at least one subject, sample the reflected radar signals, and generate a time sequence buffer of the reflected radar signals of predefined duration for vital signs processing, wherein the time sequence buffer comprises at least 60 to 120 samples;

a signal processor, configured to maintain the buffer and to perform signal processing comprising: source separation decomposition of pre-processed buffered signals via singular spectrum analysis; spectral computation of separated components; component weighting of decomposed components; forming a probability density function from weighted components; forming adaptive harmonic weights of the probability density function; and computation of vital signs from a weighted probability density function, the signal processor comprising an estimation component and tracking filter, configured for estimating and tracking the vital signs, to output tracked vital signs compensated for noise and motion artifacts; and a transmitter, configured to transmit the tracked vital signs to a display device for observation by at least one of: a subject; a system user; and a caregiver.

6. The system according to claim 5, wherein said vital signals are selected from the group consisting of: heart rate (HR); respiratory rate (RR); heart rate variability (HRV); heart rate interval (HRI); respiration amplitude (RA); respiration amplitude variability; respiration rate variability (RRV); ballistocardiogram (BCG); BCG amplitude variability; pulse wave velocity (PWV); blood pressure (i.e. MAP, systolic and diastolic); vascular resistance; body temperature; pulse pressure variability; stroke volume; stroke variability; and any combination thereof.

7. The system according to claim 5, wherein said source separation module comprises at least one component selected from the group consisting of:

a decomposition component, configured for decomposing non-mirrored signals data to spectral components; and a singular spectral analysis (SSA) component, configured for component weighting of said decomposed components.

8. The system according to claim 5, wherein said estimation component and tracking filter comprises at least one component selected from the group consisting of:

an estimation component, configured for identifying vital signs from spectral content of the selected decomposed component; and a tracking component, configured for extracting heart rate (HR) signal and respiration rate (RR) signal output.

* * * * *